United States Patent
Ketharanathan (12) 
(10) Patent No.: US 7,022,348 B2
(45) Date of Patent: Apr. 4, 2006

(54) METHOD OF CREATING BIOLOGICAL AND BIOSYNTHETIC MATERIAL FOR IMPLANTATION

(76) Inventor: Vettivetpillai Ketharanathan, 192 The Avenue, Parkville, Victoria (AU) 3052

(*) Notice: Subject to any disclaimer, the term of this patent is extended or adjusted under 35 U.S.C. 154(b) by 333 days.

(21) Appl. No.: 10/450,577

(22) PCT Filed: Dec. 14, 2001

(86) PCT No.: PCT/AU01/01619

§ 371 (c)(1),
(2), (4) Date: Jun. 16, 2003

(87) PCT Pub. No.: WO02/49687

PCT Pub. Date: Jun. 27, 2002

(65) Prior Publication Data

US 2004/0030407 A1 Feb. 12, 2004

(30) Foreign Application Priority Data

Dec. 20, 2000 (AU) .................................. PR2173

(51) Int. Cl.
*A61K 35/44* (2006.01)

(52) U.S. Cl. .................................. 424/569; 623/11.11

(58) Field of Classification Search ................ 424/569; 623/11.11
See application file for complete search history.

(56) References Cited

U.S. PATENT DOCUMENTS

| | | |
|---|---|---|
| 3,966,401 A | 6/1976 | Hancock et al. |
| 4,319,363 A | 3/1982 | Ketharanathan |
| 4,466,139 A | 8/1984 | Ketharanathan |
| 4,648,881 A | 3/1987 | Carpentier et al. |
| 4,681,588 A | 7/1987 | Ketharanathan |
| 4,798,611 A | 1/1989 | Freeman, Jr. |
| 4,820,626 A | 4/1989 | Williams et al. |
| 5,632,778 A | 5/1997 | Goldstein |
| 5,746,775 A | 5/1998 | Levy et al. |
| 5,843,181 A | 12/1998 | Jaffe et al. |
| 5,931,969 A | 8/1999 | Carpentier et al. |

FOREIGN PATENT DOCUMENTS

| | | |
|---|---|---|
| WO | WO 87/02880 | 5/1987 |
| WO | WO 96/28196 | 9/1996 |
| WO | WO 98/04299 | 2/1998 |

OTHER PUBLICATIONS

Zilla et al., Biotechnol. Appl. Biochem., vol. 40, 2004, pp. 57-66.*
Derwent Abstract Accession No. 42142C & JP 55034064 (Nitta Gelatin KK) Mar. 10, 1980. See the abstract.
Derwent Abstract Accession No. 76114C & JP 55118745 (Mitsubishi Rayon KK) Sep. 11, 1980. See the abstract.
Carpentier A., et al, (1971) Utilisation de biopolymeres dans la construction de protheses valvulaires cardiaques, C.R. Acad. Sc. Paris, vol. 272, No. 1, series D, 178-179.
Derwent Abstract for AU-004308 (Ketharanathan) (corresponding to AU-64816/80 and WO 82/00091; copy of WIPO document WO 82/00091 attached).
Vardaxis, N.J. et al. (1994) Chemical and physical properties of collagen implants influence their fate in vivo as evaluated by light and confocal microscopy, Journal of Biomedical Materials Research, vol. 28, 1013-1025.
Derwent Abstract for AU-001955 (Ketharanathan) (corresponding to AU-35532/84 and WO 85/01651; copy of WIPO document WO 85/01651 attached).
Burns, P. et al (1989) Performance of a New Vascular Xeno Prosthesis, ASAIO transactions, vol. 35, No. 3, 214-218.
Harriger, M.D. et al. (1997) Glutaraldehyde crosslinking of collagen substrates inhibits degradation in skin substitutes grafted to athymic mice, Journal of Biomedical Materials Research, vol. 35, No. 2, 137-145.

* cited by examiner

*Primary Examiner*—James Ketter
(74) *Attorney, Agent, or Firm*—Stevens & Showalter LLP (57) ABSTRACT

A method of creating an implantation material from biological and tissue engineered biosynthetic and biological tissue of autogenic, allogenic and xenogenic origin suitable for implantation into humans or animals as surgical and vascular prostheses. The resultant material inhibits in vivo calcification and provides a non-porous biomatrix which is impervious to angiogenesis and tissue ingrowth and suitable for the adhesion and retention of transplanted living cells such as endothelial cells, without the need for additional extracellular matrix protein coating. The method, which incorporates a gradual increase in glutaraldehyde concentration from 0% to no more than 5% weight/volume in a pH which is gradually changed from acid to alkaline at room temperature, maintains the micro-architecture and the cellular lining of the material. Additionally flexibility, compliance and haemo-compatibility along with strength and durability can be varied according to the end use. The glutaraldehyde penetrates the material gradually and completely, cross linking the collagenous components of the tissue.

35 Claims, 3 Drawing Sheets

METHOD OF CREATING BIOLOGICAL AND BIOSYNTHETIC MATERIAL FOR IMPLANTATION

BACKGROUND TO THE INVENTION

1. Field of the Invention

The present invention relates to a method of creating biological and biosynthetic material suitable for implantation to replace or augment damaged, diseased or absent tissues, structures or organs, of particular but by no means exclusive application in the treatment of autogenic, allogenic or xenogenic material of mammalian origin, to maintain a microarchitectural organization and inhibit in vivo calcification, tissue ingrowth and transmural angiogenesis. In one embodiment, as may be determined by the end use, transplanted living cells can be attached and retained under in vivo conditions.

2. Description of Related Art

Tissue stabilization and fixation using, for example, glutaraldehyde to impart strength, neutralize antigenic sites and sterilize biosynthetic and biological tissue for human implantation has been described previously. U.S. Pat. Nos. 4,319,363, 4,466,139 and 4,681,588 (Ketharanathan) disclose the processing of biosynthetic and biological material at a constant concentration of glutaraldehyde and at a constant pH in a static fluid environment in order to impart strength and durability, neutralize antigenic sites and sterilize the material. U.S. Pat. No. 3,966,401 (Hancock and Fogarty) describes a method of pressurizing tissues, such as those of a heart valve, with a tanning fluid such as glutaraldehyde, to within the physiological range, and releasing the pressure such that natural tissue retains flexibility. On the other hand U.S. Pat. No. 4,798,611 (Freeman) discloses a method of sterilizing, imparting compliance and reducing antigenecity by gamma radiating xenog nic material at a 1 vel of 2 to 8 megarads following treatment with a cross linking agent, for example, glutaraldehyde.

In vivo calcification has been reported in implanted glutaraldehyde treated biological tissue prostheses, particularly heart valve prostheses. In vivo micro-calcification was demonstrated in the wall of the material of U.S. Pat. No. 4,466,139 when used as a vascular conduit in dogs, though the calcification did not cause the material to fail. Storage in 50% alcohol prior to implantation reduced but did not eliminate the degree of calcification. A number of methods have been instituted in an effort to reduce or eliminate calcification. U.S. Pat. No. 4,648,881 (Carpentier et al.) describes a method of inhibiting calcification in biological tissue by the use of phosphate deficient solution, and U.S. Pat. No. 5,931,969 (Carpentier et al.) discloses treating at least partially fixed tissue in a heated treatment solution and inducing tissue/solution movement for between 15 and 60 days. In U.S. Pat. No. 5,843,181 (Jaffe and Hancock) a method is disclosed whereby biological tissue is made substantially acellular by exposure to at least one buffered solution with a pH in the range of 5 to 8 prior to fixation. U.S. Pat. No. 5,746,775 (Levy and Hirsch) discloses the inhibiting of in vivo calcification by subjecting tissue to an aqueous solution of 60 to 80% lower aliphatic alcohol containing an anti-calcification agent for at least 20 minutes following glutaraldehyde pre-treatment.

Various methods of pre-treatment of substrates with extracellular matrix proteins to emulate a protein surface, in an effort to promote growth, attachment and retention of living transplanted cells onto the surface of synthetic materials, have been documented. For example, coating polyester graft material with human plasma and fibrin gel for the attachment of endothelial cells on synthetic vascular graft surfaces to provide at least 50% confluence is disclosed in U.S. Pat. No. 4,820,626 (Williams and Jarrell). U.S. Pat. No. 5,632,778 (Goldstein) describes a method of killing native cello in interstitial collagen, removing potentially immunogenically active soluble molecules and subsequently treating the acellular tissue with extracellular substances and transplanting allogenic or autologous cells prior to implantation of the graft material.

Considerable attention has been paid to the appropriate pore size of synthetic materials for implantation in order to promote healing or biolisation via tissue ingrowth and more recently for transmural angiogenisis to promote endothelialisation. An unwanted aspect is the uncontrolled nature of tissue ingrowth particularly in vascular conduits of 6 mm internal diameter and less which causes lumenal narrowing, thrombosis and occlusion with subsequent graft failure.

SUMMARY OF THE INVENTION

The present invention provides a method of creating an implantation material from mammalian autogenic, allogenic or xenogenic tissue, said tissue comprising between 20% and 80% and preferably 40% collagen by weight, said method involving:

treating said tissue with a cross linking agent for a time period of between 30 minutes and 6 hours, including varying said cross linking agent concentration from an initial concentration of from 0% to 0.25% weight/volume to a final concentration of from 0.5% to 5% weight/volume over said time period and varying said cross linking agent pH from an initial pH of from 1 to 3 to a final pH of from 5 to 8 over said time period.

Preferably the method includes treating said tissue with said cross linking agent for a time period of approximately 2.5 hours.

Preferably said method includes progressively increasing said cross linking agent concentration and said pH over said time period.

Preferably said initial concentration is approximately 0%, and preferably said final concentration is approximately 2.5% weight/volume.

Preferably said initial pH is approximately 1.5, and preferably said final pH is approximately 7.4.

The tissue may be autogenic, allogenic or xenogenic material of, for example, human, ovine, bovine and porcine origin. The tissue may be tissue engineered biological material or material tissue engineered on a durable or degradable scaffold in a surrogate animal or by tissue culture systems in the laboratory. The tissue may be naturally occurring biological material such as ureters, pleura and blood vessels. The tissue may be of any configuration including tubular, sheet-like or three dimensional.

Preferably the cross linking agent is glutaraldehyde.

The material is preferably treated in a circulating fluid bath or a rotating drum. In a circulating bath, tubular material may be attached to a flow system such that the fluid flows through the lumen of each tube at a rate of 200 to 400 mL per minute and preferably 300 mL per minute. Preferably the method additionally includes, after said time period, treating said tissue with a cross linking agent (preferably a fresh solution thereof) at a concentration of from 0.5% to 5% (preferably 2.5%) weight/volume and a pH of from 5 to 8 (preferably 7.4), at a temperature of from 20° C. to 27° C. (preferably 25° C.), for a further time period of from 1 hour to 5 days (preferably 48 hours).

Preferably the tissue and cross linking agent solution is maintained at a temperature of from 20° C. to 27° C. but preferably approximately 25° C.

The configuration of said tissue is preferably maintained during treating by means of a compressible template to which the tissue is, preferably, either untethered, or tethered at only one end to allow movement of the material on said template.

Thus, microarchitectural alignment of the tissue is maintained without damaging the tissue.

Preferably said method includes sterilizing said tissue after said tissue has been cross linked, preferably either chemically, or by gamma irradiation in, preferably, 15 to 30 kilograys (kgys) and preferably 25 kgys.

Optionally the method includes immersing the tissue prior to sterilization in 2% weight/volume hydrogen peroxide for between 30 minutes and 1.5 hours but preferably approximately 1 hour.

Optionally the method includes incubating the tissue in glycine 5% weight/volume prior to gamma irradiation sterilization, for 2 to 24 hours and preferably for 12 hours.

Preferably the method includes storing said material in 50% volume/volume ethyl alcohol (i.e. ethanol) for a minimum of three weeks and preferably three months prior to implantation.

Thus, the treating of the tissue in this manner has been found to provide a material with an intact microarchitecture and cellular lining which inhibits in vivo calcification, tissue ingrowth and tranemural angiogenesis, and provides a microenvironment for the adhesion of transplanted living cells. Additionally, haemocompatibility, compliance and flexibility can be varied according to the desired end use by varying the process within the functional range.

The present invention also provides an implantation material created by the method described above.

BRIEF DESCRIPTION OF FIGURES

In order that the present invention may be more clearly ascertained, a preferred embodiment will now be described, by way of example, by reference to the accompanying figures, in which.

DETAILED DESCRIPTION

The current invention is based on the surprising discovery that by subjecting autogenic, allogenic and xenogenic tissue engineered biosynthetic and biological material or naturally occurring biological material to a gradual increase in the concentration of a cross linking agent such as glutaraldehyde and a gradual change in pH from acid towards alkaline, in combination with a dynamic fluid environment, preferably, a storage period of at least three weeks in 50% volume/volume ethanol after processing would provide a non-porous biomatrix with an intact microarchitecture which is impervious to tissue ingrowth and angiogenisis, would inhibit in vivo calcification, and would be suitable for the attachment and retention of transplanted living cells. Additionally, flexibility and compliance could be controlled by the gradual penetration of cross linking agent into the biosynthetic or biological material which is untethered or only tethered at one end to a compressible template during processing.

The resultant material, which has a durable biological microarchitecture and a surface that is lined with stabilized cells, for example fibroblasts on tissue engineered material and urothelium lining mammalian ureters, has an affinity for transplanted living cells and an ability to retain them under required biological conditions. Transplanted living cells are more likely to interact with the naturally occurring extracellular matrix (ECM) proteins of these cellular linings via many cellular binding sites, each of which may have more than one protein ligand, than to single ECM or derivatives of ECM which are used to coat polyester and polytetrafluoroethylene material to aid in the adhesion of endothelial cells. It is postulated that the ECM binding sites are still recognized and available for cell attachment by transplanted cells even though the biomatrix has been cross linked with glutaraldehyde. In the case of biosynthetic material the tissue engineered biological interface is presented to the living environment, the synthetic component being an endoskeletal structure only and never in contact with living structures.

The characteristics of the material can be varied for specific applications or for specific materials by th variation of the param ters of the time, percentage glutaraldehyde and pH within the functional range. For example in the case of autogenic tissue created in the laboratory, glutaraldehyde is utilized to arrest tissue proliferation at the optimal level, whereas in non autogenic tissue glutaraldehyde renders the material non-immunogenic. The degree of flexibility, compliance and durability can be varied by degree and intensity of dynamic processes.

Thus, in a method of creating implantation material by treating autogenic, allogenic and xenogenic tissue (such as tissue engineered biosynthetic and biological material and naturally occurring biological tissue in tubular, flat sheet and three dimensional configurations for surgical implantation) according to a preferred embodiment of the present invention, excess tissue is first removed from the exterior of the tissue.

The tissue is then tethered to a compressible template such that movement of the tissue on the template is not restricted. In the case of tubular tissue, the tissue is left untethered to a compressible mandrel The mounted tissue is placed into a rotating drum at between 10 and 20 rpm preferably 12 rpm, or into a circulating bath at approximately 25° C. If placed in a circulating bath, the tubular tissue may be attached to a flow system such that fluid flows through the lumen at approximately 300 mL per minute.

A cross linking agent in the form of glutaraldehyde is added to the drum or bath, the concentration of which is gradually increased from 0% up to a predetermined maximum of 2.5% weight/volume; the pH of the solution is gradually increased from 1.5 to 7.4 over a period of 2.5 hours.

Once the predetermined final concentration and pH of glutaraldehyde solution has been reached, the tissue is removed from the rotating drum and placed in a circulating bath of fresh solution of glutaraldehyde which is then maintained at a concentration of 2.5% weight/volume and a pH of 7.4, at a temperature of 25° C. Alternatively, if the tissue is already in the circulating bath the solution is renewed as above and if attached to the flow system, the flow system is removed and solution replaced as above. The tissue remains in the circulating bath for approximately 48 hours. The tissue is then immersed in 2% weight/volume hydrogen peroxide for one hour.

The tissue (or, now, implantation material) is then sterilized chemically in a 1% weight/volume solution of glutaraldehyde and 50% volume/volume ethanol for not less than 18 hours. Alternatively it can be sterilized in gamma radiation at 15 to 30 kgys but preferably 25 kgys.

Optionally the tissue is incubated in glycine 5% weight/volume for 2 to 24 hours, but preferably 12 hours, prior to sterilization.

Finally, the tissue is stored in 50% volume/volume ethanol for a minimum of three weeks and preferably three months.

EXAMPLE 1

The method of treating tissue according to this embodiment was applied to bovine ureters for use as vascular prostheses as follows.

Bovine ureters were collected under hygienic conditions and transported to the laboratory at 4° C. Physiological saline was pumped via the pelvic end of the ureter. The distal or bladder end was temporarily occluded and the pressure of the saline within the lumen was increased to 115 mm Hg. The diameter of the ureter at the mid point was recorded. A compr ssible silicon mandrel slightly narrower in diameter than the ureter and mounted on a blunt nosed steel introducer was inserted a traumatically into the pressure filled ureter. The metal introducer was removed. Excess tissue was removed from the exterior of the ureter. The ureter was then tethered to the silicone at one end, allowing some movement along the silicone. The mounted ureter was placed into a rotating drum at 12 rpm at a temperature of 21° C. The concentration of glutaraldehyde was gradually increased from 0 to a predetermined concentration of 2.5% weight/volume and the pH of solution increased from 1.5 to 5.9 by the addition of phosphate buffers over a period of 3 hours. Once the predetermined concentration and pH of glutaraldehyde solution were reached, the ureter was removed from the rotating drum and placed into a circulating bath of 2.5% weight/volume glutaraldehyde at 7.4 pH for 24 hours.

The material was removed from the glutaraldehyde, rinsed briefly in buffered saline and placed in 50% volume/volume ethanol. The compressible mandrel was removed and the integrity of the material was ascertained by pressure testing.

The material was chemically sterilized by soaking in a solution of 50% volume/volume ethanol in 1% glutaraldehyde for not less than 18 hours; the material was rinsed of sterilization solution with 50% volume/volume ethanol and stored in 50% volume/volume ethanol for a minimum of three weeks.

EXAMPLE 2

In vivo inhibition of calcification was assessed in greyhound dogs as follows.

Grafts of 6 mm internal diameter and not less than 10 cm in length prepared from bovine ureters according to this embodiment were implanted into the aorto-iliac position with the distal aorta to the proximal anastomosis ligated. Grafts of 4 mm internal diameter and not less than 6 cm in length were implanted as femoral interposition grafts.

No anti-coagulation or antiplatelet therapy was used.

Periodic angiograms were taken at predetermined intervals to verify patency and detect aneurysms, dilatation or stenoses. The animals were sacrificed at predetermined intervals, or at graft closure or animal distress.

Finally, macro- and microscopic examination of the explants were performed.

Figure 1:
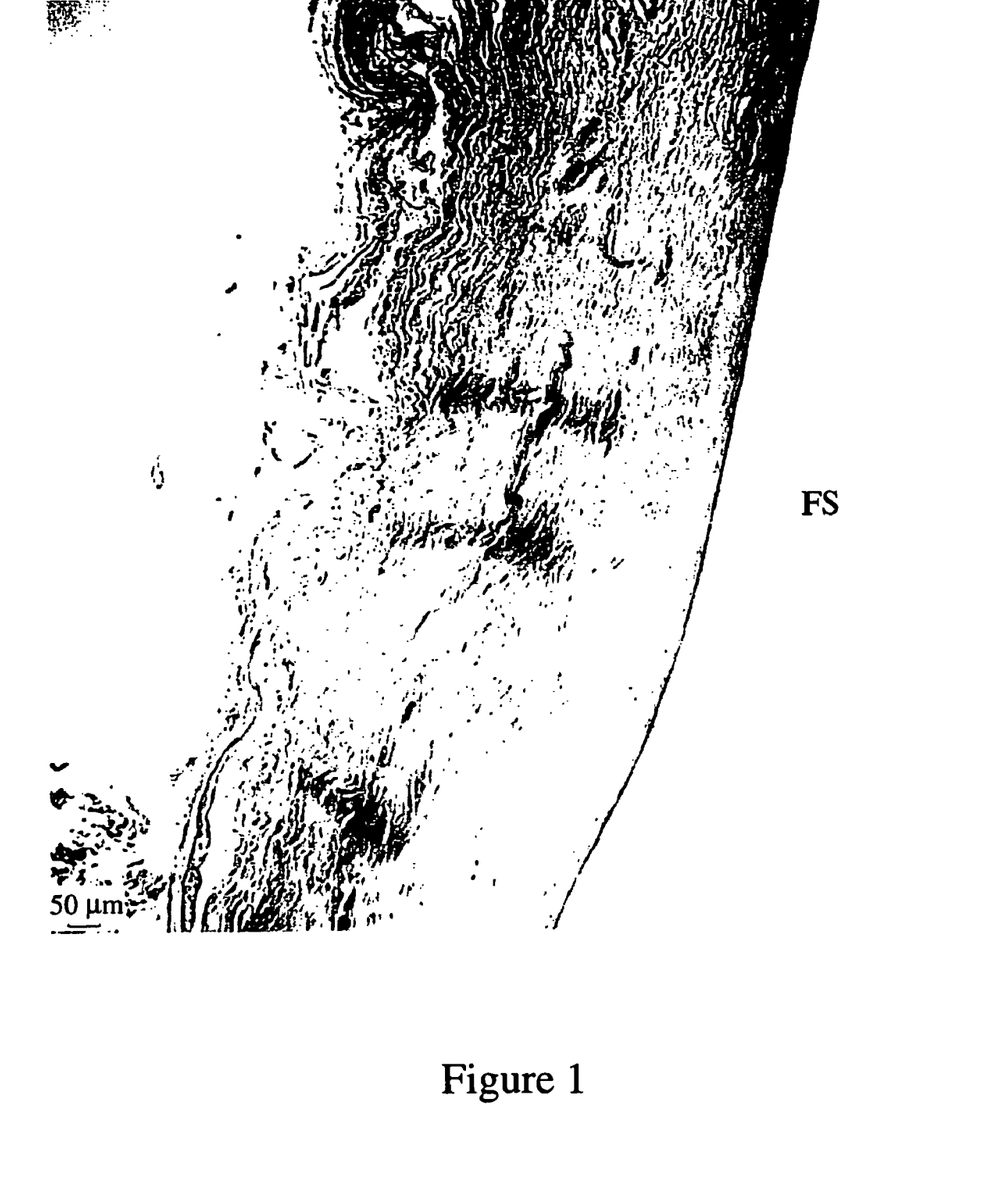
FIG. 1 is a haematoxylin and eosin stain (H & E) photomicrograph of a bovine ureter processed according to the method of a preferred embodiment of the present invention and implanted for 127 days as a vascular substitute in the canine model.

When patency, mural integrity and luminal integrity of implanted material processed by the current invention were compared with that of U.S. Pat. No. 4,466,139 neither was compromised. However, when examined microscopically, there was no calcification in 13 prostheses explanted at 1 to 18 months processed by the method of this embodiment. FIG. 1 is a haematoxylin and eosin stain (H & E) photomicrograph of a bovine ureter processed according to this embodiment and implanted for 127 days as a vascular substitute in the canine model. The graft wall is clear of microcalcification at explant. In the view shown, the flow surface FS is to the right.

Figure 2:
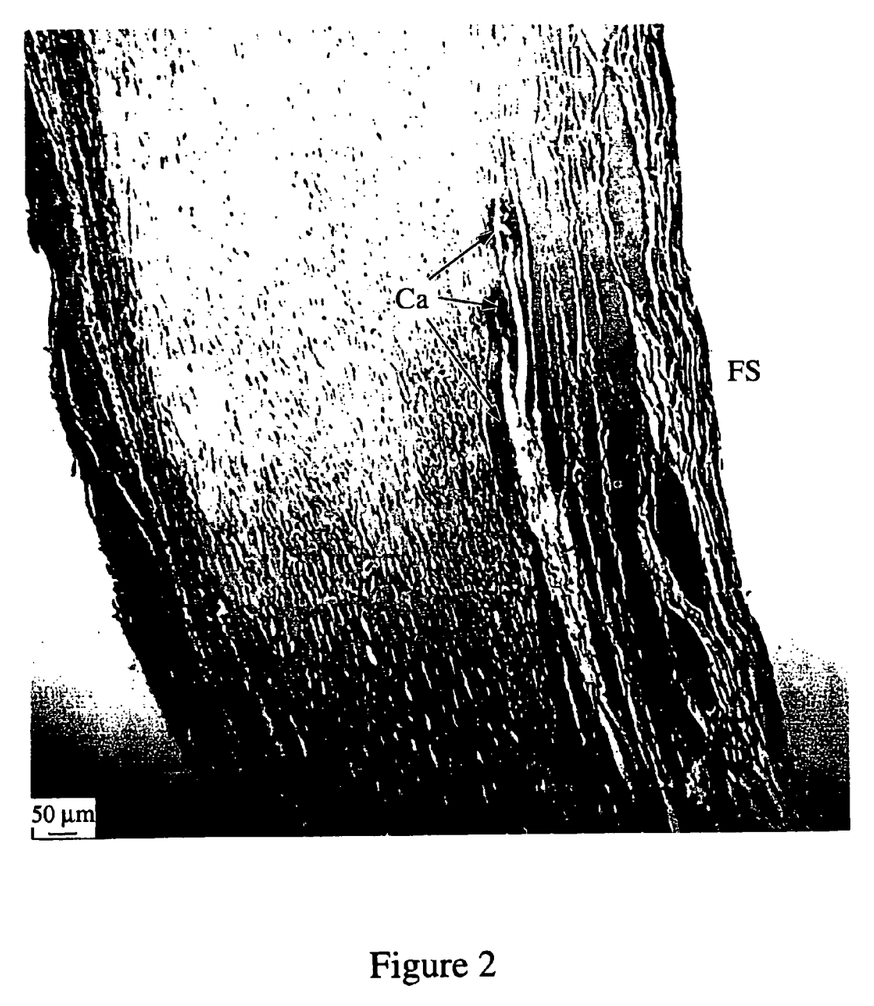
FIG. 2 is an H & E photomicrograph of a bovine ureter treated according to the method of U.S. Pat. No. 4,466,139 and implanted for 90 days as a vascular substitute in the canine model.

By contrast, at the same time period 11 of 25 prostheses (i.e. 44%) processed according to the method of U.S. Pat. No. 4,466,139 had areas of micro-calcification in the wall, primarily at the anastomotic sites. FIG. 2 is an H & E photomicrograph of a bovine ureter processed as per U.S. Pat. No. 4,466,139 and implanted for 90 days as a vascular substitute in the canine model. At explant, areas of micro-calcification (Ca) were demonstrated in the wall at the distal anastomosis. The graft was patent at explant. In the view shown, the flow surfac (FS) is to the right.

EXAMPLE 3

The attachment and adherence of human saphenous vein endothelial cells transplanted onto the surface of the processed bovine ureter were evaluated as follows.

Human saphenous vein endothelial cells were isolated, harvested and seeded using published or modified techniques. Human saphenous vein endothelial cells were isolated from inverted varicosed human saphenous vein segments obtained from the operating room and transported to the laboratory in chilled Hanks Balanced Salt Solution (HBSS, Sigma Australia) containing ampicillin (100 µg/mL), gentamycin (50 µg/mL), amphotericin B (2.5 µg/mL), L-glutamine (2.5 mM) and sodium bicarbonate (0.23%) and stored at 4° C. The ends of the veins were ligated with surgical silk. A modified enzymatic harvesting technique was utilized whereby the veins were immersed in 10 mL of 2 mg/mL collagenase (Worthington type IV, Sigma) for 10 minutes at 37° C. then vortexed on an automatic speed for 1 minute at 10 second intervals. The collected cell suspension was centrifuged at 800 g for 5 min at 4° C. and the resultant cell pellet re-suspended in 7.5 mL of M199 (Sigma Australia) containing heat inactivated foetal bovine or calf serum (FCS, CSL Australia), heparin (50 µg/mL, Sigma Australia) and endothelial cell supplement (Sigma Australia). Cells were then plated onto gelatin coated 10 cm diameter Petri dishes and incubated at 37° C. in a 5% $CO_2$, 95% air humidified incubator (NuAire USA). Cells were grown to confluence and passaged 3 times.

Endothelial cells were dissociated from the tissue culture plates using trypsin containing 0.25% Trypsin/0.2% EDTA (Sigma Australia) for 1 min. The activity of the trypsin was inactivated with 20% FCS and M199 and the cell suspension was centrifuged at 4° C., 800 g for 5 minutes. The cell pellet was re-suspended in culture medium to a cell concentration of 1×10⁶ cells/mL.

Conduits 4 mm in internal diameter and not less than 10 cm long, were filled with the cell solution and rolled (16 rotation/h) for one hour in 37° C. incubator. After seeding, the conduits were incubated at 37° C. under 5% $CO_2$. Conduit samples (1 cm) were taken after 0, 24, 48 and 72 h of incubation in order to assess percentage cell cover and cell density.

Conduits seeded with human saphenous vein endothelial cells had greater than 50% confluent cover after 72 hours incubation. The conduits were subjected to in vitro flow of media at 480 mL/min and a shear stress of 11.4 dynes/cm² for one hour delivered by an in vitro flow system consisting of a blood monitor pump (Gambro BMM10-1/3) to three seeded conduits attached to the outflow line in parallel.

Pre and post flow endothelial cell cover was determined following labelling of cells with anti CD31 antibody (PECAM). Labelled cells were detected with an alkaline phosphatase labelled streptavivdin/biotin system with a 5-bromo-4-chloro-3-indolylphosphate-nitroblue tetrazolium (BCIP/NBT) chromagen (Dako Australia).

Results

Figure 3:
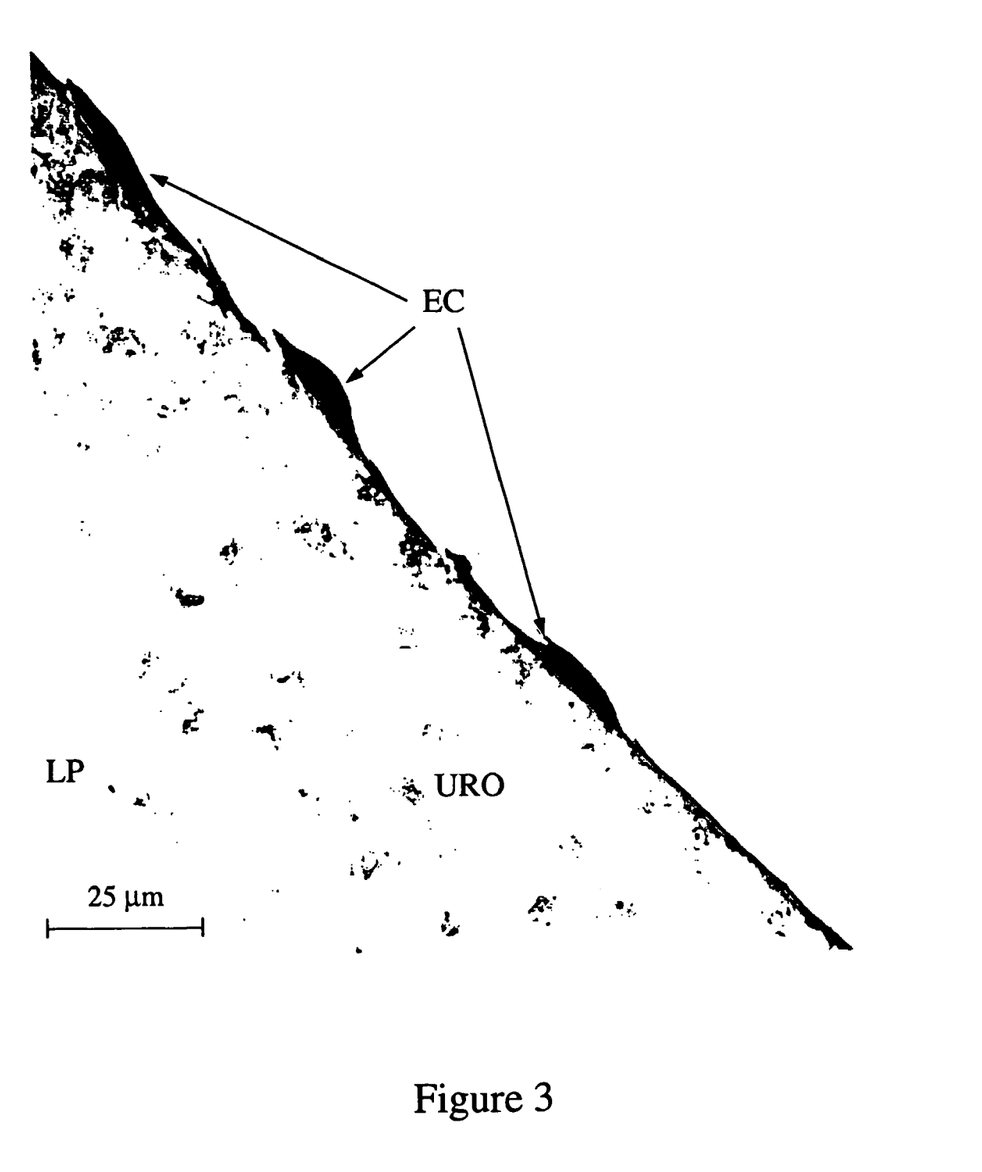
FIG. 3 is a photomicrograph of a monolayer anti CD31 labelled human saphenous vein endothelial cells attached to the flow surface of a bovine ureter that had been treated according to the method of the preferred embodiment.

Confluent monolayers of endothelial cells were firmly adherent to the biomatrix surface consisting of urothelial cells, and remained adherent under in vitro shear stresses of 11.4 dynes/cm². FIG. 3 is a photomicrograph of anti CD31 labelled cells detected with an alkaline phosphatase labelled stretavidin/biotin system with a BCIP/NBT chromagen. FIG. 3 shows a monolayer of human saphenous vein endothelial cells (EC) attached to the flow surface of a bovine ureter, processed according to this embodiment, after one hour of in vitro shear stresses of 11.4 dynes/cm². In this figure, the lamina propria is labelled LP, and the urothelium is labelled URO.

Thus, the method of this embodiment can be applied to autogenic, allogenic and xenogenic tissue to create implantation material for humans or animals to replace or augment damaged, diseased or absent tissues, structures or organs. The method can be adjusted to impart the required characteristics to biological or biosynthetic tissue for implants for specific applications. The resultant material could be implanted into the cardiovascular environment for example as a small vessel coronary or peripheral bypass graft, an artificial tissue heart valve or a stent biobarrier to prevent tissue ingrowth and hence in-stent stenosis. The non-porous and tissue impervious nature of the processed material inhibits the ingrowth of tissue and angiogenesis through the wall, one of the major causes of failure in small diameter synthetic bypass grafts. The material could also be implanted into the non-cardiovascular environment as for example an artificial skin, hernia repair patch or artificial ligament. Function of the material can be further enhanced by the addition of living cells prior to implantation. For example the addition of endothelial cells onto the flow surface of the small vessel replacement would provide anticoagulant function to prevent the blood clotting.

Modifications may be made to the invention as will be apparent to a person skilled in the art. These and other modifications may be made without parting from the ambit of the current invention, the nature which may be ascertained from the foregoing description and the figures.

The invention claimed is:

1. A method of creating an implantation material from mammalian autogenic, allogenic or xenogenic tissue, said tissue comprising between 20% and 80% collagen by weight, said method involving:
   treating said tissue with a cross linking agent for a time period of between 30 minutes and 6 hours, including varying said cross linking agent concentration from an initial concentration of from 0% to 0.25% weight/volume to a final concentration of from 0.5% to 5% weight/volume over said time period and varying said cross linking agent pH from an initial pH of from 1 to 3 to a final pH of from 5 to 8 over said time period wherein said cross linking agent is glutaraldehyde.

2. A method as claimed in claim 1, wherein said tissue comprises approximately 40% collagen by weight.

3. A method as claimed in claim 1, wherein said time period is approximately 2.5 hours.

4. A method as claimed in claim 1, including progressively increasing said cross linking agent concentration and said pH over said time period.

5. A method as claimed in claim 1, wherein said initial concentration is approximately 0%.

6. A method as claimed in claim 1, wherein said final concentration is approximately 2.5% weight/volume.

7. A method as claimed in claim 1, wherein said initial pH is approximately 1.5.

8. A method as claimed in claim 1, wherein said final pH is approximately 7.4.

9. A method as claimed in claim 1, wherein said tissue is autogenic, allogenic or xenogenic material.

10. A method as claimed in claim 1, wherein said tissue is of human, ovine, bovine or porcine origin.

11. A method as claimed in claim 1, wherein said tissue is tissue engineered biological material, material tissue engineered on a durable or degradable scaffold in a surrogate animal, or material tissue engineered by tissue culture systems in a laboratory.

12. A method as claimed in claim 1, wherein said tissue is naturally occurring biological material.

13. A method as claimed in claim 1, including treating said material in a circulating fluid bath or a rotating drum.

14. A method as claimed in claim 1, wherein said material is tubular and said method includes:
   treating said material in a circulating fluid bath or a rotating drum; and
   attaching said material to a flow system such that fluid flows through the lumen of said material at a rate of 200 to 400 mL per minute.

15. A method as claimed in claim 14, wherein that fluid flows through the lumen of said material at a rate of approximately 300 mL per minute.

16. A method as claimed in claim 1, including, after said time period, treating said tissue with a cross linking agent at a concentration of from 0.5% to 5% weight/volume and a pH of from 5 to 8, at a temperature of from 20° C. to 27° C., for a further time period of from 1 hour to 5 days.

17. A method as claimed in claim 16, including, after said time period, treating said tissue with a cross linking agent at a concentration of approximately 2.5% weight/volume.

18. A method as claimed in claim 16, including, after said time period, treating said tissue with a cross linking agent at a pH of approximately 7.4.

19. A method as claimed in claim 16, including, after said time period, treating said tissue with a cross linking agent at a temperature of approximately 25° C.

20. A method as claimed in claim 16, wherein said further time period is approximately 48 hours.

21. A method as claimed in claim 1, including maintaining said tissue and cross linking agent solution at a temperature of from 20° C. to 27° C.

22. A method as claimed in claim 21, including maintaining said tissue and cross linking agent solution at a temperature of approximately 25° C.

23. A method as claimed in claim 1, including maintaining the configuration of said tissue during treating by means of a compressible template.

24. A method as claimed in claim 23, wherein said tissue is either untethered, or tethered at only one end to allow movement of said material on said template.

25. A method as claimed in claim 1, including sterilizing said tissue after said tissue has been cross linked.

26. A method as claimed in claim 25, including immersing said tissue prior to sterilization in approximately 2% weight/volume hydrogen peroxide for between 30 minutes and 1.5 hours.

27. A method as claimed in claim 26, including immersing said tissue prior to sterilization in approximately 2% weight/volume hydrogen peroxide for approximately 1 hour.

28. A method as claimed in claim 25, including sterilizing said tissue chemically.

29. A method as claimed in claim 25, including sterilizing said tissue by means of gamma irradiation in 15 to 30 kilograys.

30. A method as claimed in claim 29, including sterilizing said tissue by means of gamma irradiation in 25 kilograys.

31. A method as claimed in claim 29, including incubating said tissue in glycine 5% weight/volume prior to gamma irradiation sterilization, for 2 to 24 hours.

32. A method as claimed in claim 31, including incubating said tissue in glycine 5% weight/volume prior to gamma irradiation sterilization, for approximately 12 hours.

33. A method as claimed in claim 1, including storing said material in 50% volume/volume ethanol for a minimum of three weeks prior to implantation.

34. A method as claimed in claim 33, including storing said material in 50% volume/volume ethanol for at least three months prior to implantation.

35. An implantation material created by means of the method of claim 1.

* * * * *

UNITED STATES PATENT AND TRADEMARK OFFICE
CERTIFICATE OF CORRECTION

PATENT NO. : 7,022,348 B2
APPLICATION NO. : 10/450577
DATED : April 4, 2006
INVENTOR(S) : Vettivetpillai Ketharanathan It is certified that error appears in the above-identified patent and that said Letters Patent is hereby corrected as shown below:

Col. 1, line 36, "radiating xenog nic material" should read --radiating xenogenic material--;
Col. 1, line 36-37, "at a 1 vel of 2" should read --at a level of 2--;
Col. 2, line 5, "killing native cello in" should read --killing native cells in--;
Col. 3, line 29, "and tranemural angiogeneis" should read --and transmural angiogeneis--;
Col. 4, line 30, "materials by th variation" should read --materials by the variation-;
Col. 4, line 31, "of the param ters of" should read --by the parameters of--;
Col. 5, line 31, "A compr ssible silicone" should read --A compressible silicone--;
Col. 5, line 33, "inserted a traumatically into" should read --inserted atraumatically into--;
Col. 6, line 31, "the flow surfac (FS)" should read --the flow surface (ES)--.

Signed and Sealed this

Fifteenth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 7,022,348 B2
APPLICATION NO. : 10/450577
DATED : April 4, 2006
INVENTOR(S) : Vettivetpillai Ketharanathan

It is certified that error appears in the above-identified patent and that said Letters Patent is hereby corrected as shown below:

Col. 1, line 36, "radiating xenog nic material" should read --radiating xenogenic material--;
Col. 1, line 36-37, "at a 1 vel of 2" should read --at a level of 2--;
Col. 2, line 5, "killing native cello in" should read --killing native cells in--;
Col. 3, line 29, "and tranemural angiogeneis" should read --and transmural angiogeneis--;
Col. 4, line 30, "materials by th variation" should read --materials by the variation-;
Col. 4, line 31, "of the param ters of" should read --by the parameters of--;
Col. 5, line 31, "A compr ssible silicone" should read --A compressible silicone--;
Col. 5, line 33, "inserted a traumatically into" should read --inserted atraumatically into--;
Col. 6, line 31, "the flow surfac (FS)" should read --the flow surface (FS)--.

This certificate supersedes Certificate of Correction issued August 15, 2006.

Signed and Sealed this

Seventeenth Day of April, 2007

JON W. DUDAS
*Director of the United States Patent and Trademark Office*